(12) United States Patent
Iizuka

(10) Patent No.: US 10,321,806 B2
(45) Date of Patent: Jun. 18, 2019

(54) ENDOSCOPE AND RIGID DISTAL END PORTION OF ENDOSCOPE

(71) Applicant: OLYMPUS CORPORATION, Tokyo (JP)

(72) Inventor: Tomoyuki Iizuka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/249,922

(22) Filed: Aug. 29, 2016

(65) Prior Publication Data

US 2016/0367114 A1  Dec. 22, 2016

Related U.S. Application Data

(63) Continuation of application No. PCT/JP2015/060191, filed on Mar. 31, 2015.

(30) Foreign Application Priority Data

Aug. 5, 2014 (JP) ................ 2014-159773

(51) Int. Cl.
*A61B 1/00* (2006.01)
*G02B 23/24* (2006.01)
(Continued)

(52) U.S. Cl.
CPC ...... *A61B 1/00098* (2013.01); *A61B 1/00078* (2013.01); *A61B 1/00096* (2013.01);
(Continued)

(58) Field of Classification Search
CPC .............. A61B 1/0008; A61B 1/00091; A61B 1/00094; A61B 1/00096; A61B 1/00163;
(Continued)

(56) References Cited

U.S. PATENT DOCUMENTS

| 3,924,608 A | 12/1975 | Mitsui |
| 5,573,494 A | 11/1996 | Yabe et al. |

(Continued)

FOREIGN PATENT DOCUMENTS

| EP | 0978251 A1 | 2/2000 |
| JP | H08-056900 A | 3/1996 |

(Continued)

OTHER PUBLICATIONS

International Search Report dated Jun. 23, 2015 issued in PCT/JP2015/060191.
(Continued)

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

An endoscope includes an operation section, an insertion section, a first space provided in a distal end portion of the insertion section, a second space sealed against an inner space of a bending portion, a communication passage communicating between the first space and the second space, and an elongated tube member having one end portion coupled with the first space and another end portion provided inside the operation section and having a through hole in a longitudinal direction.

10 Claims, 11 Drawing Sheets

(51) Int. Cl.
*A61B 1/018* (2006.01)
*A61B 1/05* (2006.01)
*A61B 1/008* (2006.01)

(52) U.S. Cl.
CPC ............... *A61B 1/018* (2013.01); *A61B 1/05* (2013.01); *G02B 23/24* (2013.01); *A61B 1/008* (2013.01)

(58) Field of Classification Search
CPC ............ A61B 1/00165; A61B 1/00167; A61B 1/0017; A61B 1/00172; A61B 1/00174; A61B 1/00177; A61B 1/00179; A61B 1/00181; A61B 1/00183; A61B 1/00186; A61B 1/00188; A61B 1/0019; A61B 1/00192; A61B 1/05; A61B 1/051; A61B 1/053; A61B 1/055; A61B 1/06; A61B 1/0607; A61B 1/012; A61B 1/015; A61B 1/018
USPC ................................ 600/129, 127, 104, 107
See application file for complete search history.

(56) References Cited

U.S. PATENT DOCUMENTS

| | | |
|---|---|---|
| 6,547,721 B1 | 4/2003 | Higuma et al. |
| 2004/0082836 A1 | 4/2004 | Hino |
| 2005/0272975 A1* | 12/2005 | McWeeney ......... A61B 1/00071 600/113 |
| 2007/0270638 A1* | 11/2007 | Kitano ............... A61B 1/00098 600/104 |
| 2008/0255424 A1* | 10/2008 | Durgin ................ A61B 1/0008 600/156 |
| 2012/0078041 A1 | 3/2012 | Kitano et al. |
| 2013/0172677 A1* | 7/2013 | Kennedy, II ........... A61B 1/051 600/112 |

FOREIGN PATENT DOCUMENTS

| | | |
|---|---|---|
| JP | H09-135809 A | 5/1997 |
| JP | 2000-107120 A | 4/2000 |
| JP | 2004-141315 A | 5/2004 |
| JP | 2007-136044 A | 6/2007 |

OTHER PUBLICATIONS

Japanese Office Action dated Mar. 1, 2016 issued in JP 2015-554925.

Extended Supplementary European Search Report dated Sep. 22, 2017 in European Patent Application No. 15 83 0618.3.

* cited by examiner

ENDOSCOPE AND RIGID DISTAL END PORTION OF ENDOSCOPE

CROSS REFERENCE TO RELATED APPLICATION

This application is a continuation application of PCT/JP2015/060191 filed on Mar. 31, 2015 and claims benefit of Japanese Application No. 2014-159773 filed in Japan on Aug. 5, 2014, the entire contents of which are incorporated herein by this reference.

BACKGROUND OF THE INVENTION

1. Field of the Invention

The present invention relates to an endoscope having, at a distal end portion of an insertion section, a raising base for switching the direction of a treatment instrument which is guided outside from a distal end opening provided in the insertion section and a rigid distal end portion of an endoscope.

2. Description of the Related Art

As a medical endoscope, there is a so-called duodenoscope, which is a side-view type endoscope (hereinafter referred to as an endoscope) having an illumination lens and an objective lens arranged on a side surface on the distal end side of an insertion section.

The endoscope is used for surgical techniques such as endoscopic retrograde cholangiopancreatography for imaging a pancreaticobiliary duct through a duodenum, or endoscopic papillotomy for removing a choledocholith (bile duct stone).

The endoscope is provided with a treatment instrument insertion channel and a raising device.

The treatment instrument insertion channel is a tubular body with a through hole for inserting a treatment instrument such as a contrast tube, a basket catheter, or a balloon catheter. The treatment instrument insertion channel is disposed inside an insertion section, along a longitudinal axis of the insertion section. A distal end of the treatment instrument insertion channel is connected to a distal end portion main body forming a distal end portion of the endoscope, and its proximal end is connected to a treatment instrument insertion opening provided in an operation section.

On the other hand, the raising device is a device for switching, to a desired direction, the direction of a treatment tool which is passed through the treatment instrument insertion channel and is guided to outside from a distal end opening provided in the distal end portion main body. Generally, the raising device is configured mainly from a raising base which is rotatably disposed to the distal end portion main body, a raising base operation lever provided in the operation section, and a raising base operation wire configured to move according to operation of the raising base operation lever and to swing the raising base.

Japanese Patent Application Laid-Open Publication No. 8-56900 discloses an endoscope which allows even a treatment instrument or the like with a narrow distal end to smoothly protrude without getting caught in a raising base operation wire, and to be easily guided by being observed near the center of an observation field of view.

According to the endoscope, an observation window is provided in one of left and right half portions on side surfaces of a distal end of an insertion section, and a treatment instrument raising base to be swung in the front-back direction by remote operation is provided in the other half portion. A pair of inner and outer walls which are in contact with both side surfaces of the treatment instrument raising base in the swinging range of the treatment instrument raising base are formed to the distal end of the insertion section, and a distal end of an operation wire to be remotely operated is disposed on a back side of the outer wall surface, and motion of a distal end of the operation wire is transmitted to the treatment instrument raising base by a driving force transmission member disposed penetrating the outer wall.

That is, as shown in FIG. 1 of Japanese Patent Application Laid-Open Publication No. 8-56900, at a distal end portion main body forming a distal end portion of the insertion section of the endoscope, the observation window and an illumination window are arranged in the longitudinal axis direction of the distal end portion main body, the treatment instrument raising base is rotatably provided between an inner wall and an outer wall facing each other across the longitudinal axis, a raising base drive lever is provided in a raising base drive chamber formed in a recessed manner on an outer side surface of the outer wall, on the other side of the longitudinal axis, and an operation wire is fixedly installed to the raising base drive lever by a pin.

Moreover, an opening portion of the raising base drive chamber is blocked in a liquid-tight manner by a sealing lid, and an insulating plastic cover is externally attached to the distal end portion main body. Furthermore, a liquid, such as a body fluid, is prevented from entering into a raising base accommodating chamber from outside by providing an O-shaped ring to the raising base drive lever.

Also, the observation window and the illumination window are provided in a liquid-tight manner to the distal end portion main body. As a result, a liquid is prevented from entering from outside into the distal end portion main body through the observation window and the illumination window.

SUMMARY OF THE INVENTION

An endoscope according to an aspect of the present invention includes an operation section; an insertion section extending from the operation section, and including a distal end portion provided on a distal end side and a bending portion provided consecutively to the distal end portion; a first space provided in the distal end portion; a second space, provided in the distal end portion and sealed against an inner space in the bending portion, where at least an image pickup unit is disposed; a communication passage provided in the distal end portion, and configured to communicate between the first space and the second space; and an elongated tube member having a through hole in a longitudinal direction, and having one end portion coupled with the first space and another end portion provided inside the operation section.

A rigid distal end portion in an endoscope according to an aspect of the present invention is a rigid distal end portion in an endoscope which is disposed on a distal end of an insertion section of the endoscope, and includes: a first space; a second space where at least an image pickup unit is disposed; and a communication passage communicating between the first space and the second space, wherein the first space and the second space are sealed against a space disposed behind the rigid distal end portion, and a distal end portion of an elongated tube member is coupled with the first space, the tube member having a rear end portion provided in an operation section of the endoscope and having a through hole in a longitudinal direction.

DETAILED DESCRIPTION OF THE PREFERRED EMBODIMENT(S)

Figure 1:
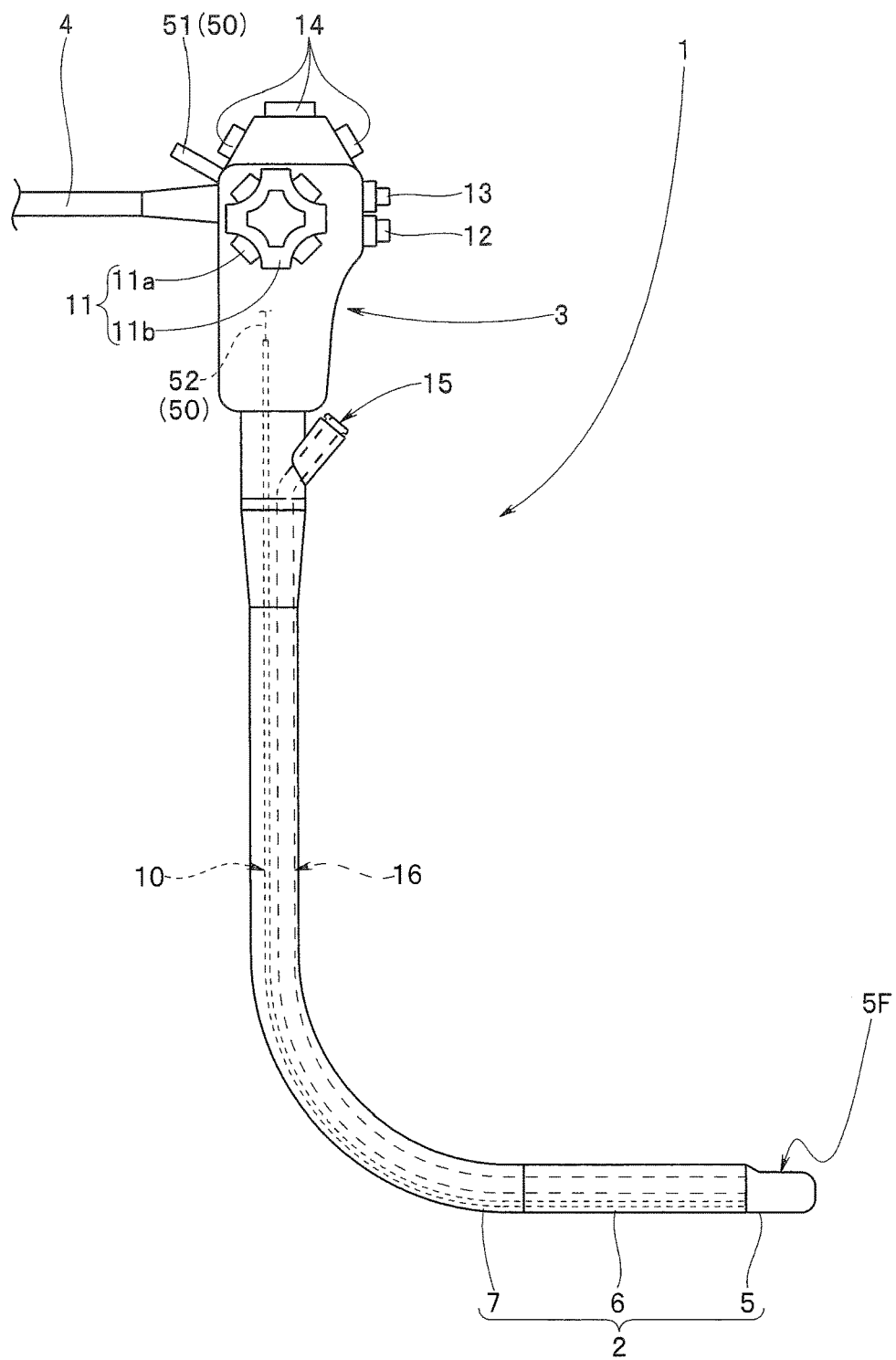
FIG. 1 is a diagram describing a side-view type endoscope.

Hereinafter, an embodiment of the present invention will be described with reference to the drawings.

Note that, in each of the drawings used in the following description, the scale of display of each structural component is made different such that each structural component is large enough to be recognized in the drawing. Also, the present invention is not limited to the modes shown in the drawings with respect to the number of structural components, the shapes of the structural components, the proportion of the sizes of the structural components, and the relative positional relationship of respective structural components.

In the following, an endoscope of the present embodiment is a side-view type endoscope.

As shown in FIG. 1, an endoscope 1 is configured by including an insertion section 2 to be inserted into a subject, an operation section 3 provided on the proximal end side of the insertion section 2, and a universal cord 4 extending from the operation section 3.

The operation section 3 of the endoscope 1 is provided with a bending operation device 11, an air/water feeding button 12, a suction button 13, a raising base operation lever 51 constituting a raising device 50 described later, and various operation switches 14.

The operation switches 14 are a freeze switch configured to generate a freeze signal, a release switch configured to generate a release signal at a time of performing photographing, an observation mode switching switch configured to issue an instruction to switch an observation mode, and the like.

The operation section 3 is provided with a treatment instrument insertion opening 15 for introducing a treatment instrument (not shown) into a living body. One end side of a treatment instrument insertion channel 16 is connected to the treatment instrument insertion opening 15, and another end of the treatment instrument insertion channel 16 is connected to a distal end portion main body (see the reference sign 20 in FIG. 8), described later, constituting a distal end portion 5 of the insertion section 2. The treatment instrument insertion channel 16 is a flexible tubular body, and is disposed inside the insertion section 2, along a longitudinal axis of the insertion section 2.

The reference sign 10 is a tube member, and is a flexible resin tube having a longitudinal through hole. The tube member 10 is a dual-purpose tubular body described later, and is disposed inserted in the insertion section 2 along the longitudinal axis of the insertion section 2. A proximal end surface of the tube member 10 is provided inside the operation section 3, and a raising base operation wire 52 constituting the raising device 50 is inserted through the tube member 10.

A mid-portion of the raising base operation wire 52 is disposed inside the tube member 10. A distal end of the raising base operation wire 52 is guided out of the tube member 10, and is connected to a raising base operation arm (see the reference sign 53 in FIG. 5) constituting the raising device 50. A proximal end of the raising base operation wire 52 extends from a proximal end of the tube member 10, and is connected to the raising base operation lever 51 through a link mechanism or the like, not shown.

The insertion section 2 extending from the operation section 3 is configured from a distal end portion 5, a bending portion 6, and a flexible tube portion 7 which are provided consecutively in this order from the distal end side.

For example, the flexible tube portion 7 is configured by including a spiral tube, a mesh tube covering the spiral tube, and a heat shrinkable tube forming an outermost layer, which are not shown. The bending portion 6 is configured by including a set of bending pieces (see the reference sign 6a in FIG. 3) which are configured to bend in four direction of up, down, left, and right, a metal mesh tube (see the reference sign 6b in FIG. 3) covering the set of bending pieces 6a, and a bending rubber (see the reference sign 6c in FIG. 3), which is an outer skin.

Figure 3:
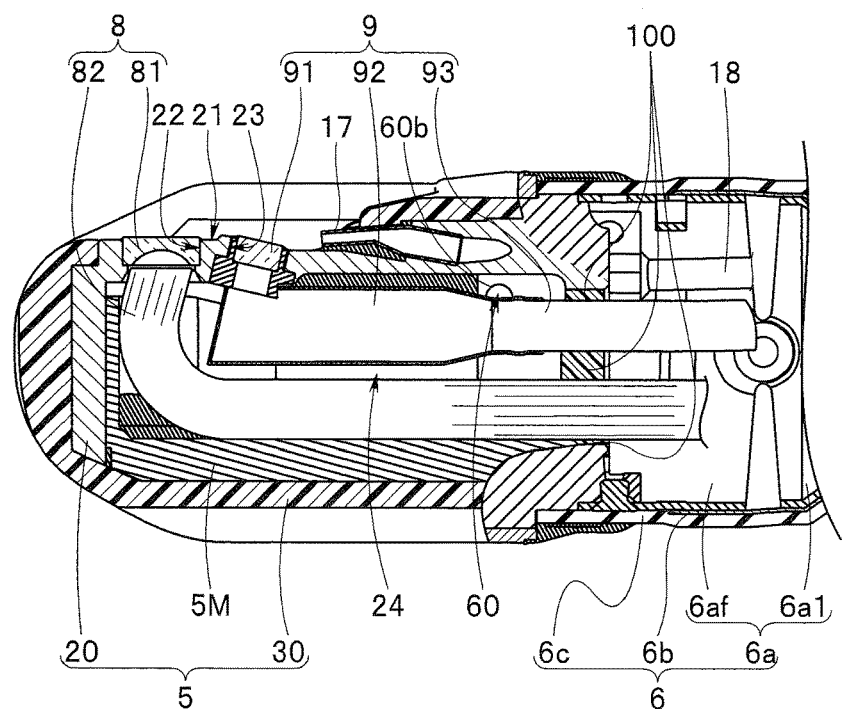
FIG. 3 is a cross-sectional diagram along a line Y3-Y3 in FIG. 2.

The reference sign 6af in FIG. 3 is a distal end bending piece, the reference sign 6a1 is a first intermediate bending piece, and the bending pieces are a part of a plurality of bending pieces constituting the set of bending pieces.

The bending portion 6 is configured to be bent in an upward direction or a downward direction by rotation operation of an upward/downward bending knob 11a of the bending operation device 11 provided in the operation section 3, and to be bent in a left/right direction by rotation operation of a left/right bending knob 11b.

A flat surface portion 5F is provided on one side surface, for example, an upper side surface, of the distal end portion 5 of the endoscope 1.

The upper side surface is a surface corresponding to the upward bending direction of the bending portion 6.

Figure 2:
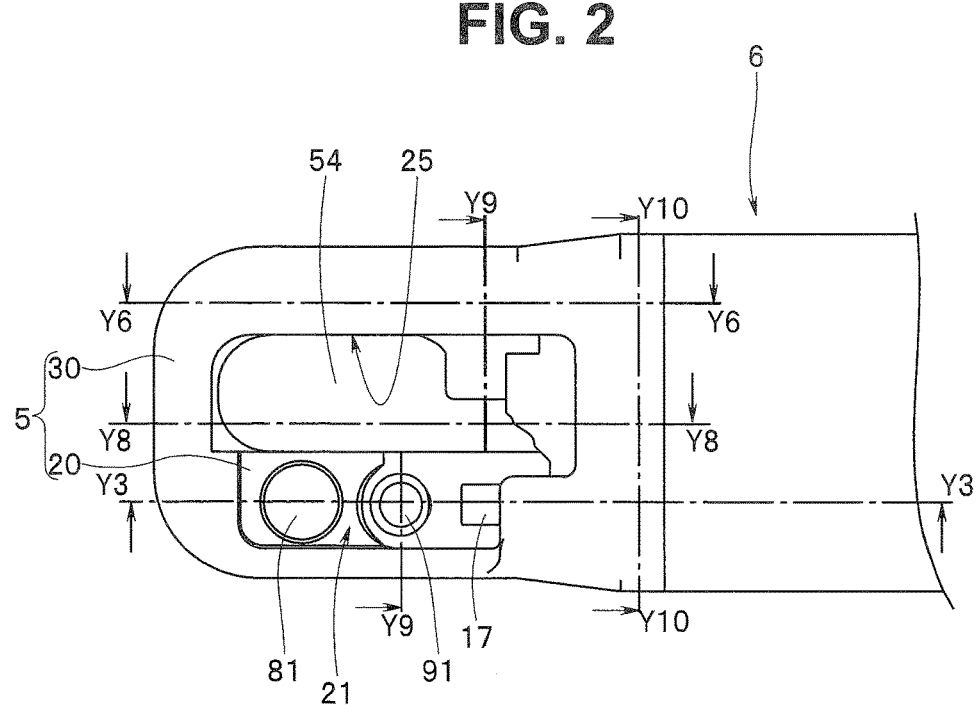
FIG. 2 is a diagram showing a distal end portion in FIG. 1, and is a front view of a flat surface portion of the distal end portion.

As shown in FIGS. 2 and 3, for example, the distal end portion 5 is configured by including a distal end portion main body 20, and a cover member 30.

The distal end portion main body 20 is a rigid member of metal, for example, and the cover member 30 is a rigid member of resin, for example.

The cover member 30 is integrally fixed, in a liquid-tight manner, to the distal end portion main body 20 excluding the flat surface portion 5F and the proximal end portion side of the distal end portion main body 20.

Figure 4:
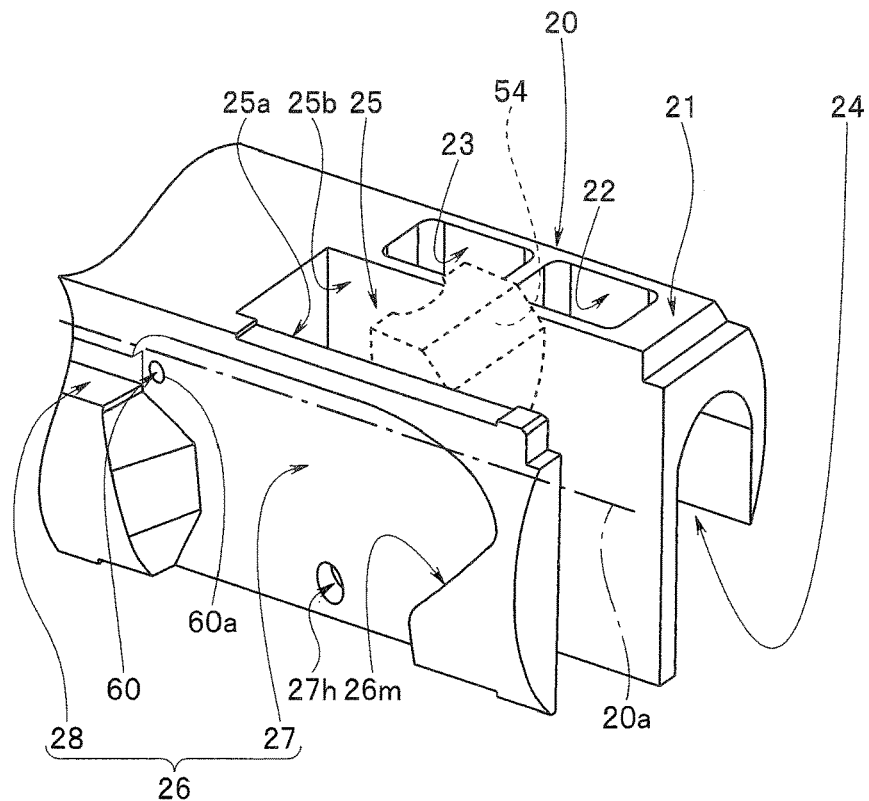
FIG. 4 is a diagram describing a configuration of a distal end portion main body.

As shown in FIG. 4, the distal end portion main body 20 is configured by including a flat surface 21 mainly constituting the flat surface portion 5F, an illumination window hole 22 and an observation window hole 23 provided as openings at predetermined positions on the flat surface 21, a recessed portion 24 for optics, a raising base space 25, and an arm accommodating chamber 26.

The raising base space 25 is a recessed portion provided at a center portion of the distal end portion main body 20, and is a groove with a predetermined depth from a distal end surface of the distal end portion main body 20, and includes wall surfaces 25a, 25b which face each other across a longitudinal axis 20a. A raising base 54 constituting the raising device 50 is to be rotatably disposed in the raising base space 25.

The raising device 50 is mainly configured from the raising base operation lever 51, the raising base operation wire 52, the raising base operation arm 53, and the raising base 54, which are described above. The raising base operation lever 51, the raising base operation arm 53, and the raising base 54 are rigid members, and are of metal or resin.

The recessed portion 24 for optics is a groove that is formed along the longitudinal axis 20a. The recessed portion 24 for optics is provided on the left side of the raising base space 25 when the distal end portion main body 20 is seen from the distal end surface side. The illumination window hole 22 and the observation window hole 23 are formed in a manner communicating with the recessed portion 24 for optics.

The arm accommodating chamber 26 is a recessed portion provided on the right side of the raising base space 25 when the distal end portion main body 20 is seen from the distal end surface side, and an opening 26m of the arm accommodating chamber 26 is formed on the right side surface.

The arm accommodating chamber 26 is configured by including a recessed portion 27 for an arm and a recessed portion 28 for a fixing tool.

Figure 5:
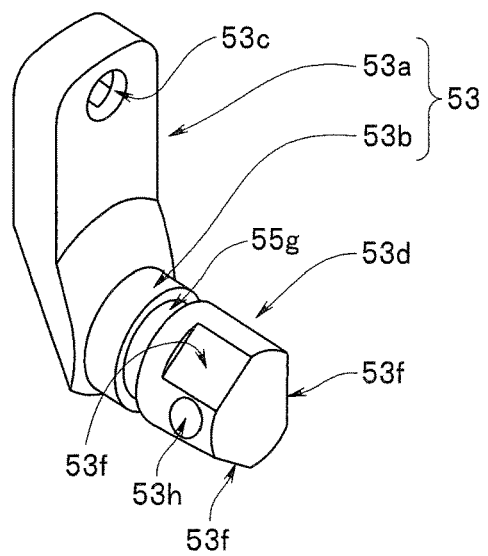
FIG. 5 is a diagram describing a raising base operation atm.

An arm main body 53a of the raising base operation arm 53 shown in FIG. 5 is to be disposed in the recessed portion 27 for an arm. For this purpose, an opening which is a shaft hole 27h shown in FIG. 4 is formed to a bottom surface of the recessed portion 27 for an arm. The shaft hole 27h is a through hole for communicating between the recessed portion 27 for an arm and the raising base space 25, and a shaft portion 53b of the raising base operation arm 53 is rotatably disposed in the shaft hole 27h.

Figure 10:
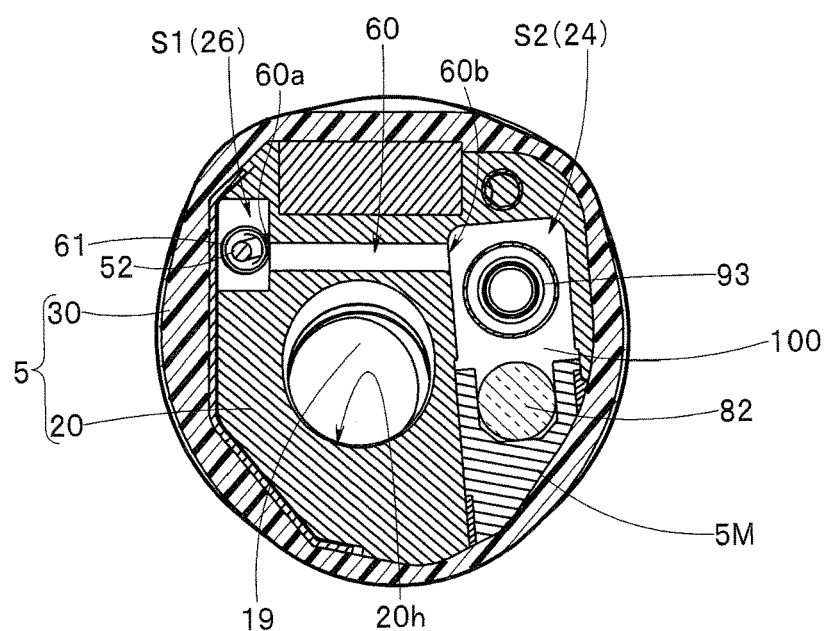
FIG. 10 is a cross-sectional diagram along a line Y10-Y10 in FIG. 2.

The reference sign 60a is a first opening 60a of a communication passage 60. Additionally, as shown in FIG. 10 described later, the communication passage 60 is a through hole having the first opening 60a at the recessed portion 27 for an arm and a second opening 60b at the recessed portion 24 for optics.

As shown in FIG. 5, the raising base operation arm 53 is L-shaped, and is configured by including the arm main body 53a, and the shaft portion 53b. A wire fixing portion 53c, which is a through hole, in which a distal end portion of the raising base operation wire 52 is to be fixedly installed is provided at an end surface side of the arm main body 53a.

Figure 6:
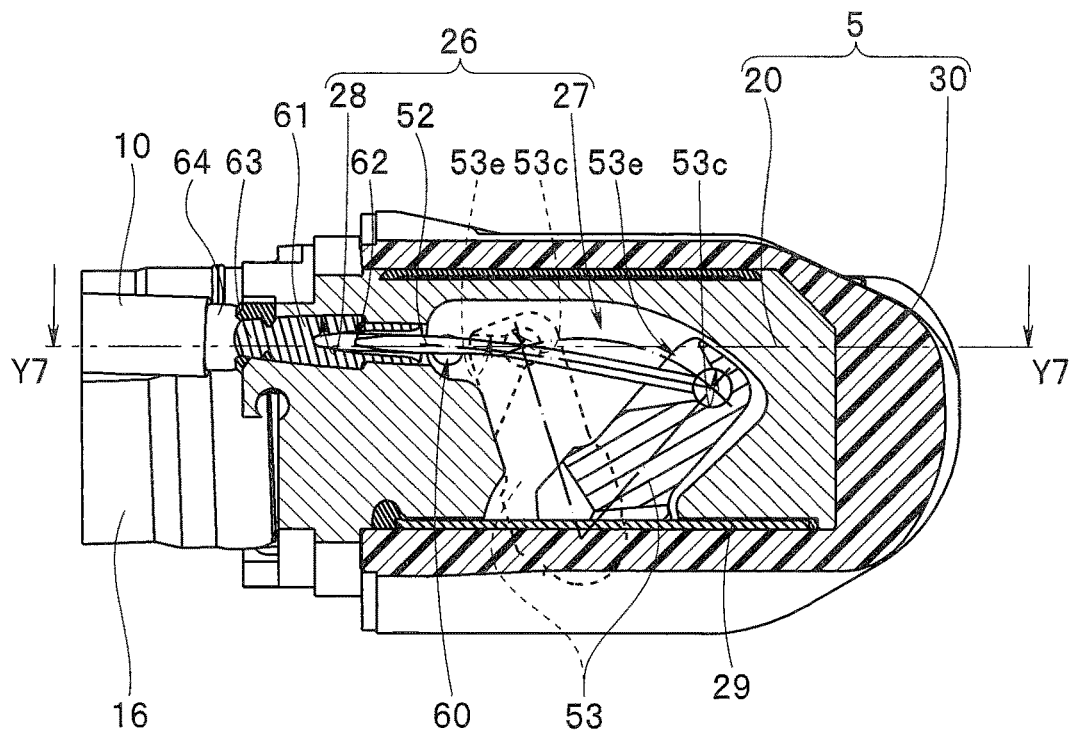
FIG. 6 is a cross-sectional diagram along a line Y6-Y6 in FIG. 2.
Figure 7:
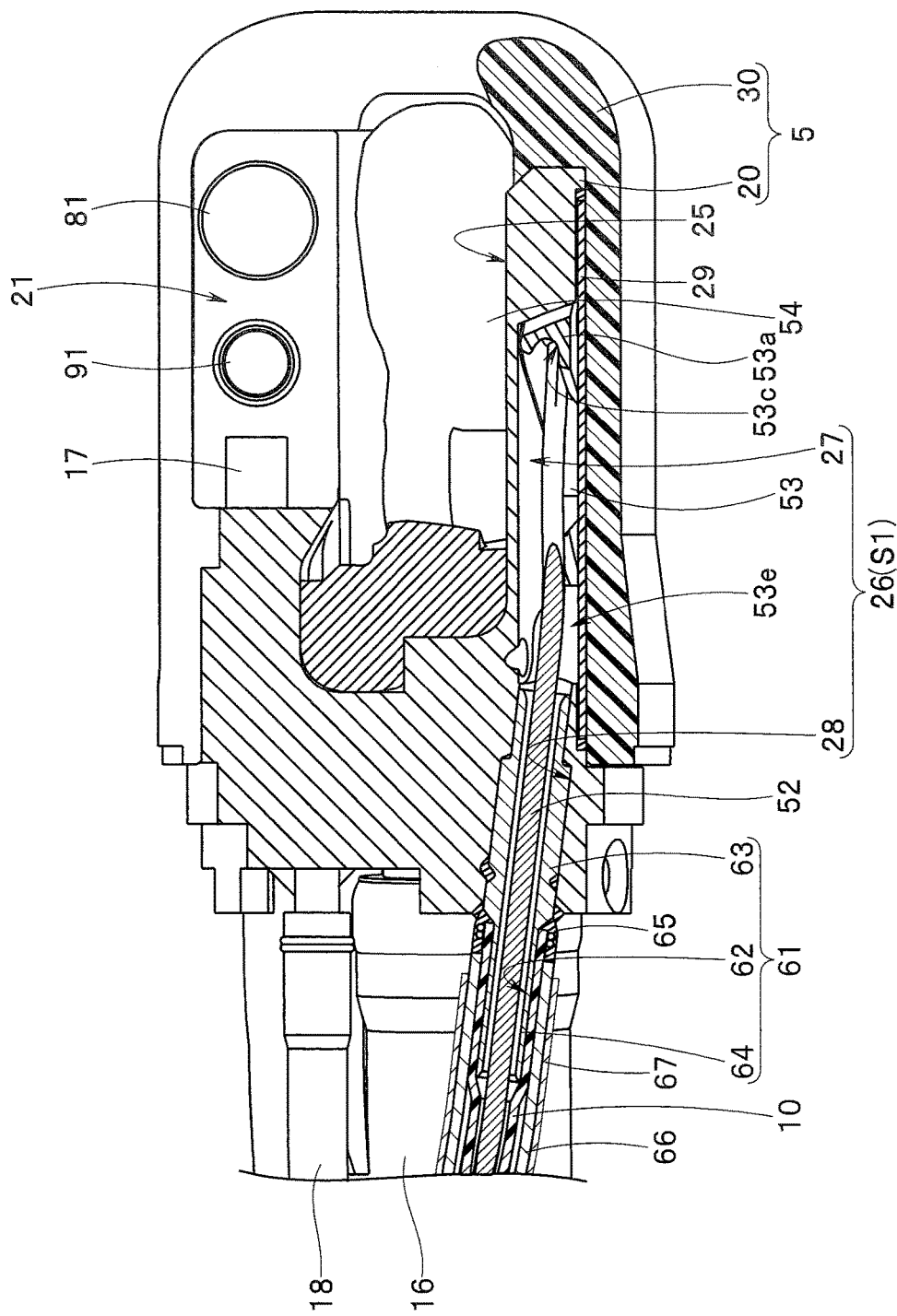
FIG. 7 is a diagram including a cross-sectional diagram along a line Y7-Y7 in FIG. 6.

The raising base operation wire 52 is guided to the recessed portion 27 for an arm through a through hole 62 formed to a pipe-shaped fixing tool 61 that is fixedly installed inside the recessed portion 28 for a fixing tool, as shown in FIGS. 6 and 7. A main body portion 63 of the fixing tool 61 is integrally fixed inside the recessed portion 28 for a fixing tool by soldering, adhesion, screw fastening or the like.

A proximal end portion of the fixing tool 61 is configured as a tube member coupling portion 64 to which a distal end portion of the tube member 10 is to be fixedly installed. The tube member coupling portion 64 protrudes into an inner space of the bending portion 6 by a predetermined amount from a proximal end surface of the distal end portion main body 20.

The tube member 10 is integrally fixed to the fixing tool 61 by an adhesive 65 after being externally fitted to the tube member coupling portion 64. The adhesive 65 is applied to around the distal end portion of the tube member 10 and the proximal end surface of the distal end portion main body 20. As a result, an opening on the proximal end side of the recessed portion 28 for a fixing tool in which the fixing tool 61 is disposed is sealed against an inner space of the bending portion 6 by the adhesive 65.

Additionally, as the method of sealing, there is also a method of filling the gap between the main body portion 63 and the recessed portion 28 for a fixing tool by an adhesive, a sealant or the like. In this case, the tube member 10 and the tube member coupling portion 64 may be fixed by being tied together by a string member such as a fishing gut, instead of using an adhesive.

The shape of the through hole 62, of the end portion on the side of the tube member coupling portion 64, is tapered, and the inner diameter which is great on the proximal end opening side is reduced toward a mid-portion. According to this configuration, the distal end of the raising base operation wire 52 guided out of the tube member 10 is smoothly inserted into the through hole 62, and is guided to the recessed portion 27 for an arm after passing through the through hole 62.

The distal end of the raising base operation wire 52 is passed through the inside of a guide hole 53e and is disposed at the wire fixing portion 53c. The distal end of the raising base operation wire 52 is fixed, by a solder applied to the wire fixing portion 53c or by brazing, for example, in such a way that it will not fall out of the arm main body 53a.

Additionally, as shown in FIG. 6, the guide hole 53e is substantially fan-shaped, and is formed to gradually spread out from the wire fixing portion 53c toward one side surface. The reference sign 66 is a dual-purpose tube protection member, which is a coil member for protecting the tube member 10, and is disposed on the outer circumferential side of the tube member 10. A distal end portion of the dual-purpose tube protection member 66 is fixedly installed near the proximal end surface of the distal end portion main body 20 by the adhesive 65.

Furthermore, an outer surface of the dual-purpose tube protection member 66 is covered with a tube protection member 67. The tube protection member 67 prevents the dual-purpose tube protection member 66 from being damaged by coming into contact with other internal components at the time of bending operation of the bending portion 6, by covering the dual-purpose tube protection member 66 at least in the range of the bending portion 6 (see FIG. 7).

Figure 9:
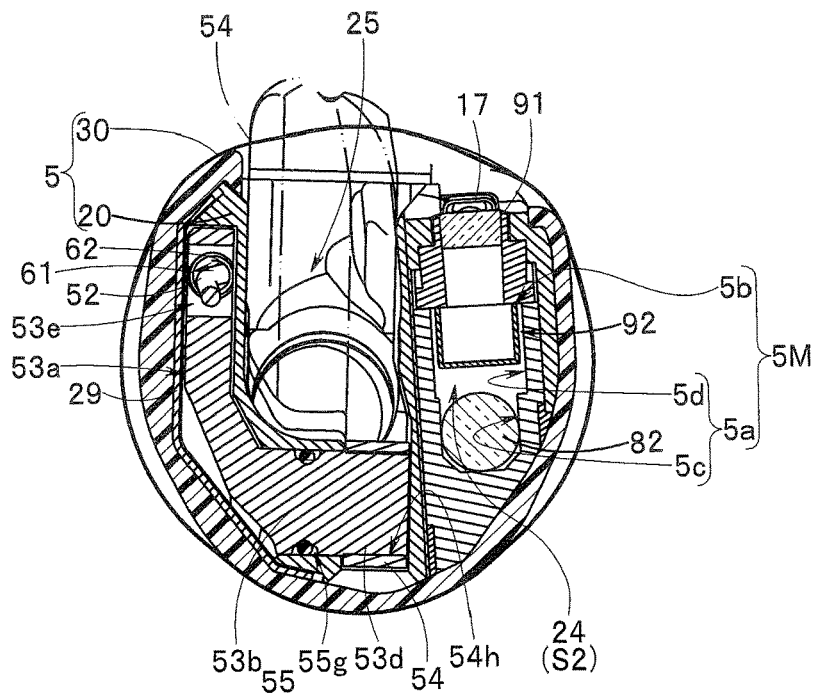
FIG. 9 is a cross-sectional diagram along a line Y9-Y9 in FIG. 2.

The cross-section of the shaft portion 53b shown in FIG. 5 is circular, and the shaft portion 53b is rotatably disposed in the shaft hole 27h. As shown in FIG. 9, an O-shaped ring 55 is provided on the shaft portion 53b. The O-shaped ring 55 comes into close contact with the entire inner circumference of the shaft hole 27h to maintain liquid tightness.

The O-shaped ring 55 is disposed in a circumferential groove 55g shown in FIG. 5. The side more to the end surface than the circumferential groove 55g of the shaft portion 53b is a raising base coupling portion 53d. For example, three flat surface portions 53f serving as rotation detents are provided at regular intervals on the outer circumferential surface of the raising base coupling portion 53d. The reference sign 53h is a detent hole, and the distal end portion side of a locking pin is disposed in the detent hole 53h.

As shown in FIG. 9, in a state of being disposed inside the shaft hole 27h, the shaft portion 53b protrudes from the first wall surface 25a into the raising base space 25. Then, the raising base coupling portion 53d is disposed inside a coupling hole 54h of the raising base 54 disposed in the raising base space 25.

Figure 8:
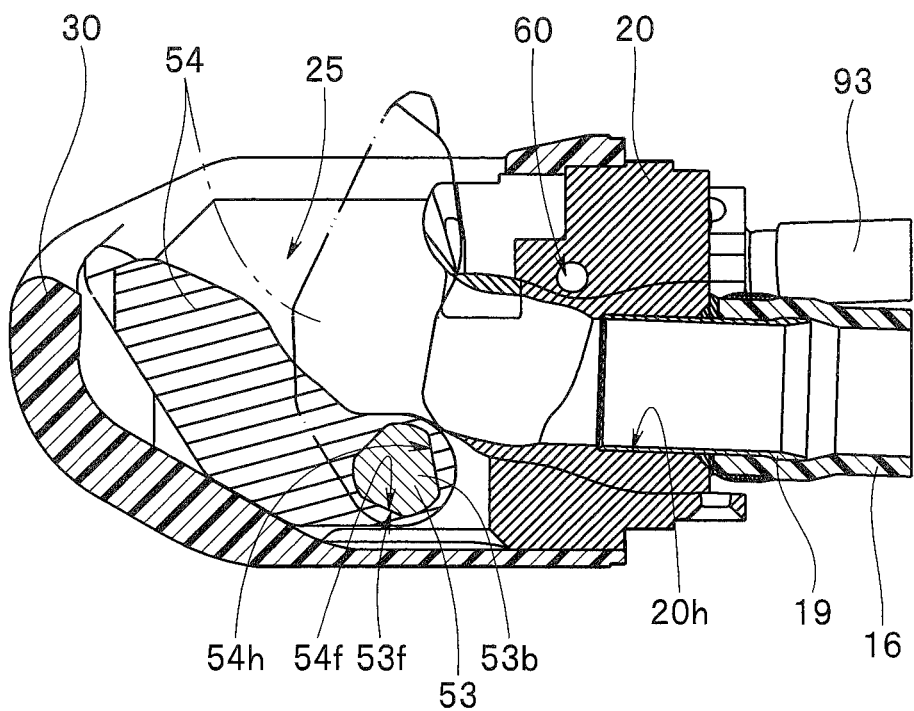
FIG. 8 is a cross-sectional diagram along a line Y8-Y8 in FIG. 2.

As shown in FIG. 8, flat abutting surfaces 54f are provided in the coupling hole 54h in relation to the flat surface portions 53f. Also, a hole (not shown) for a locking pin in which the locking pin is to be disposed is formed near the coupling hole 54h. In a coupled state, the locking pin, not shown, is fixedly installed in the hole for a locking pin and the detent hole.

As a result, as shown in FIGS. 8 and 9, the raising base coupling portion 53d protruding in the raising base space 25 is fixedly installed in the coupling hole 54h, which is a through hole provided in the raising base 54, and the raising base operation arm 53 and the raising base 54 are integrally configured.

Moreover, as shown in FIG. 8, a distal end portion of the treatment instrument insertion channel 16 into which a treatment instrument or the like is to be inserted is fixedly installed in a proximal end portion of a channel pipe sleeve 19 which is fixedly installed in the distal end portion main body 20. The channel pipe sleeve 19 is fixedly installed in a pipe sleeve hole 20h, which is a through hole formed at a predetermined position along the longitudinal axis of the distal end portion main body 20. The pipe sleeve hole 20h does not reach the communication passage 60, and is provided with an opening on the side of the raising base space 25 while taking into account the position where the raising base 54 is to be disposed.

As shown in FIGS. 6 and 9, the opening 26m of the arm accommodating chamber 26 is covered and blocked by the cover member 30 after being sealed by a lid member 29. Also, the O-shaped ring 55 provided on the shaft portion 53b is in close contact with the entire inner circumference of the shaft hole 27h while maintaining liquid tightness. Moreover, as shown in FIG. 7, the opening, on the proximal end side, of the recessed portion 28 for a fixing tool where the fixing tool 61 is disposed and the distal end portion of the tube member 10 are sealed against the inner space of the bending portion 6 by the adhesive 65. Also, the proximal end surface of the tube member 10 is provided inside the operation section 3.

As a result, the arm accommodating chamber 26 of the distal end portion main body 20 is provided, in the distal end portion 5, as a first closed space S1 which is sealed against the inner space of the bending portion 6.

As shown in FIGS. 2 and 3, an illumination lens 81, which is an illumination window constituting an illumination optical system 8, is fixed to the illumination window hole 22 in a liquid-tight manner. Also, an observation lens 91, which is an observation window constituting an observation optical system 9, is fixed to the observation window hole 23 in a liquid-tight manner. The reference sign 17 is a nozzle. A fluid, such as water or air, is injected from the nozzle 17 toward the illumination lens 81 and the observation lens 91. The reference sign 18 is an air/water feeding pipe.

The illumination optical system 8 is configured by mainly including the illumination lens 81, and a light guide fiber bundle 82. A distal end surface of the light guide fiber bundle 82 faces a proximal end surface of the illumination lens 81. A proximal end portion of the light guide fiber bundle 82 extends from an opening of the recessed portion 24 for optics, on the proximal end side, and is disposed at a predetermined position inside an endoscope connector (not shown) after passing through the insides of the insertion section, the operation section, and the universal cord.

The observation optical system 9 is configured by mainly including the observation lens 91, an image pickup apparatus 92, and a signal cable 93. The image pickup apparatus 92 is configured by including a plurality of optical lenses, an image pickup device, and a substrate on which electronic components are mounted, which are not shown.

The observation lens 91 constitutes the distal end side of the image pickup apparatus 92. Like the light guide fiber bundle 82, a proximal end portion of the signal cable 93 extends from the opening of the recessed portion 24 for optics, on the proximal end side, and is disposed at a predetermined position inside the endoscope connector after passing through the insides of the insertion section, the operation section, and the universal cord.

The reference sign 60b is the second opening of the communication passage 60. The reference sign 5M is a distal end portion constituent member, and is integrally fixed inside the recessed portion 24 for optics by an adhesive or the like, as shown in FIGS. 3 and 9. An optical system accommodating portion 5a and an image pickup apparatus support portion 5b are provided in the distal end portion constituent member 5M.

A light guide arrangement portion 5c where the light guide fiber bundle 82 is to be disposed, and an image pickup apparatus accommodating space 5d where the image pickup apparatus 92 is to be disposed are provided in the optical system accommodating portion 5a. As shown in FIGS. 9 and 10, the light guide fiber bundle 82 is disposed along a bottom surface of the light guide arrangement portion 5c. The image pickup apparatus 92 is disposed in the image pickup apparatus accommodating space 5d in a manner separated from the light guide fiber bundle 82.

As shown in FIGS. 3 and 9, openings on the distal end side and the lower side of the recessed portion 24 for optics where the distal end portion constituent member 5M is provided are covered and blocked by the cover member 30. Also, the opening on the proximal end side of the recessed portion 24 for optics is coated and blocked by a sealing member 100 in a state in which the distal end portion constituent member 5M is provided. The sealing member 100 fills the surrounding of the light guide fiber bundle 82 extending from the opening on the proximal end side of the recessed portion 24 for optics, the surrounding of the signal cable 93, a proximal end surface of the distal end portion constituent member 5M, and an inner surface of the cover member 30.

As a result, the recessed portion 24 for optics of the distal end portion main body 20 is provided, in the distal end portion 5, as a second closed space S2 which is sealed against the inner space of the bending portion 6.

Moreover, as shown in FIG. 10, the first closed space S1 and the second closed space S2 are communicated with each other by the communication passage 60.

A working of the endoscope configured in the above manner will be described.

For example, when examining the inside of a bile duct, a surgeon first inserts the distal end portion 5 of the insertion section 2 of the endoscope 1 inside the duodenum. The surgeon then inserts a treatment instrument into the treatment instrument insertion channel 16 through the treatment instrument insertion opening 15 provided in the operation section 3 of the endoscope 1. The surgeon causes the treatment instrument to pass through the channel 16 and above the raising base 54, and to protrude to outside the distal end portion 5 by a predetermined amount.

Here, the surgeon operates the raising base operation lever 51. The raising base operation wire 52 inside the tube member 10 is moved according to the operation of the lever 51. Then, according to the movement of the raising base operation wire 52, the arm main body 53a of the raising base operation arm 53 moves inside the first closed space S1, around the shaft portion 53b, from a state shown by the solid line in FIG. 6 to a state shown by the dotted line.

Also, the raising base 54, which is integrally fixed to the raising base operation arm 53, is rotated in the same manner inside the raising base space 25 according to the rotation of the arm main body 53a, thereby changing the direction of the treatment instrument, and the treatment instrument is made to face the bile duct at a distal end, for example. The surgeon inserts the treatment instrument into the bile duct, and performs examination or the like.

After the examination, the surgeon removes the endoscope 1 from the living body.

After the examination, the endoscope is cleaned and disinfected. At the time of cleaning/disinfecting, water leakage detection is performed to investigate whether a hole is opened to the insertion section 2 or the like. That is, pressurized air is supplied from the endoscope connector (not shown) of the endoscope into the universal cord 4, the operation section 3, and the insertion section 2. In the water leakage detection, the pressurized air is supplied from the opening at the proximal end of the tube member 10 through the inside of 10 into the first closed space S1 provided in the distal end portion 5, and is also supplied through the communication passage 60 into the second closed space S2 provided in the distal end portion 5.

As a result, in addition to investigation of opening of a hole to the insertion section 2, investigation may be reliably performed in relation to separation of an adhesive layer between the illumination lens 81 and the distal end portion main body 20, or presence/absence of damage to the illumination lens 81, or separation of an adhesive between the lens frame of the observation lens 91 and the distal end portion main body, presence/absence of damage, or the like.

As described above, the first closed space S1 and the second closed space S2, which are sealed against the inner space of the bending portion 6, are provided inside the distal end portion 5, and the first closed space S1 and the second closed space S2 are communicated by the communication passage 60. In addition, one end of the tube member 10 is communicated with the first closed space S1, and the proximal end is disposed inside the operation section.

According to the configuration, the tube member 10 serves as both a guide tube through which the raising base operation wire 52 is to be inserted and a fluid tube configured to supply pressurized air. As a result, an inconvenience of a powder lubricant or the like applied to a set of bending pieces constituting the bending portion 6 entering the first closed space S1 and the second closed space S2 may be solved without increasing the diameter of the insertion section 2, or changing the configuration of the raising device 50. Moreover, at the time of water leakage detection, pressurized air may be supplied into the first closed space S1 and the second closed space S2 so that detection of water leakage inside the insertion section 2 may be performed more reliably.

Additionally, the endoscope 1 described above is a side-view type endoscope. However, the endoscope is not limited to the side-view type endoscope, and is applicable as a front-view type endoscope having the raising base provided in the treatment instrument insertion channel.

Furthermore, the tube member 10 of the embodiment described above is a flexible resin tube, and has a longitudinal through hole. The tube member 10 is not limited to a resin tube having a longitudinal through hole, and it may alternatively be a resin tube having a plurality of small through holes which communicate between the inside of a longitudinal through hole and the outside of the outer circumferential surface, for example. By using the resin tube with a plurality of small holes as the tube member 10, moisture inside the second closed space S2 may be released to the entire region in the inner space of the endoscope 1 through the communication passage 60, the first closed space S1, and the small through holes of the tube member 10, and the lenses 81, 91 may be prevented from being clouded.

Furthermore, a configuration is also possible where only the resin tube is not provided, or where the resin tube and the protection tube are not provided, or where only the protection tube is not provided. In such cases, there is a possibility of a lubricant entering from the gap of the coil. However, because the gap of the coil is sufficiently small, entering of the lubricant may be sufficiently prevented. The tube member 10 may be made thinner by adopting such a configuration.

Furthermore, also in a case where the first space is not completely sealed, entering of a lubricant from the bending tube portion into the second space may be made difficult by sufficiently narrowing the communication passage or by changing the direction of the channel from a long axis direction to a substantially perpendicular direction.

Figure 11A:
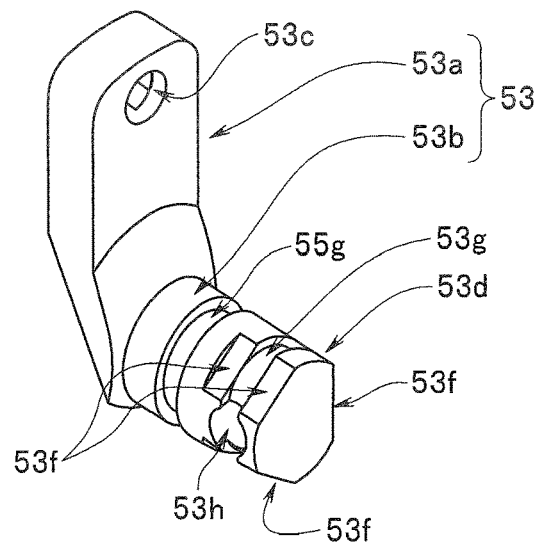
FIG. 11A is a diagram describing another example confignration of the raising base operation arm.
Figure 11B:
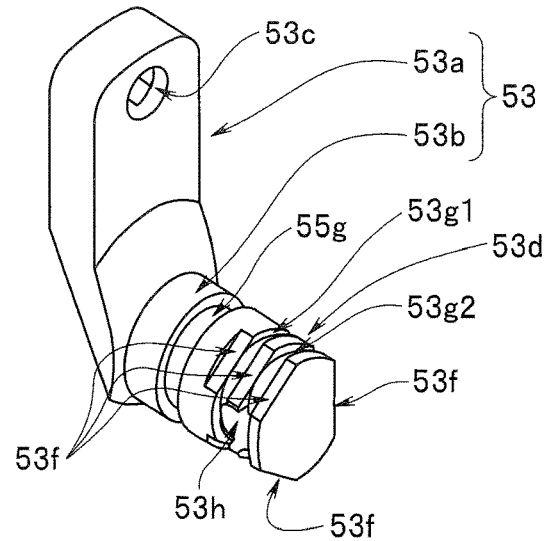
FIG. 11B is a diagram describing another example confignration of the raising base operation arm.
Figure 11C:
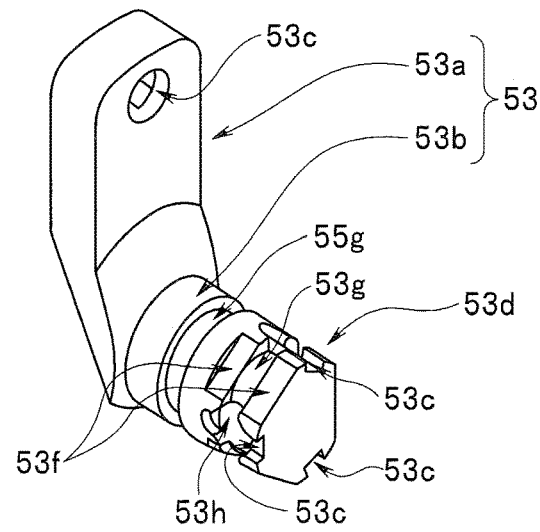
FIG. 11C is a diagram describing another example confignration of the raising base operation arm.
Figure 12A:
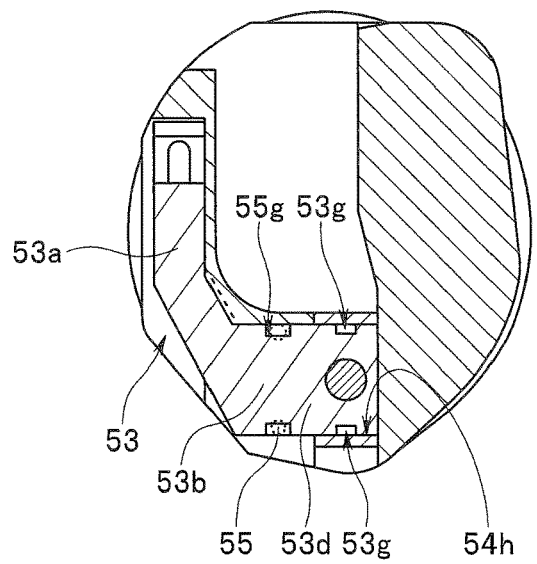
FIG. 12A is a diagram describing a state in which a raising base coupling portion is disposed inside a coupling hole of a raising base.
Figure 12B:
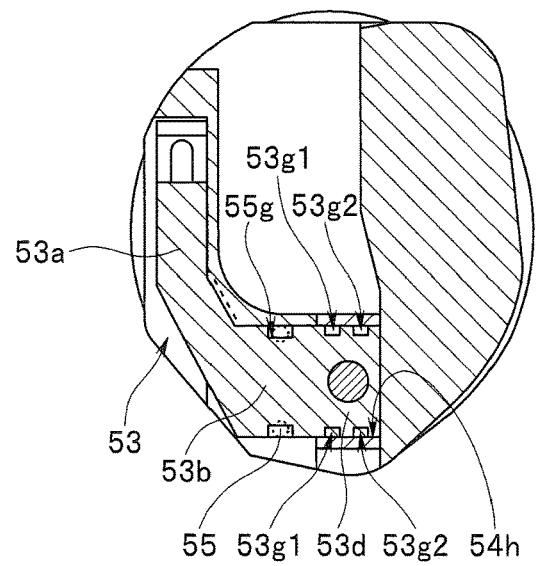
FIG. 12B is a diagram describing a state in which a raising base coupling portion is disposed inside a coupling hole of a raising base.

Furthermore, a groove as shown in FIG. 11A, 11B or 11C may be formed to the raising base coupling portion 53d, of the raising base operation arm 53, having the flat surface portions 53f, and the raising base coupling portion 53d may be coupled to the coupling hole 54h of the raising base 54, as shown in FIG. 12A or 12B, so as to increase the cleaning performance.

In FIG. 11A, one circumferential groove 53g dividing each flat surface portion 53f into two is provided at the center of the flat surface portions 53f. The width dimension of the circumferential groove 53g is set as appropriate taking the area of the flat surface portion 53f into account. In FIG. 11B, two circumferential grooves 53g1, 53g2 dividing each flat surface portion 53f into three are provided. The width dimensions of the circumferential grooves 53g1, 53g2 are the same, for example, and are set as appropriate taking the area of the flat surface portion 53f into account. In FIG. 11C, in addition to the one circumferential groove 53g dividing each flat surface portion 53f into two, a plurality of orthogonal grooves 53h orthogonal to the circumferential groove 53g are provided. The orthogonal grooves 53h are each provided between the respective flat surface portions 53f. The width dimension of the orthogonal grooves 53h is set as appropriate taking the area of the flat surface portion 53f into account.

According to the configuration described above, as shown in FIGS. 12A and 12B, when cleaning water or rinsing water is supplied into the raising base space 25, the liquid enters the gap between the raising base coupling portion 53d and the coupling hole 54h of the raising base 54, and after passing through the gap, the liquid flows in the circumferential groove 53g, the first circumferential groove 53g1, the second circumferential groove 53g2, or the orthogonal grooves 53h to swiftly wash out the dust or the like in the gap.

Figure 13A:
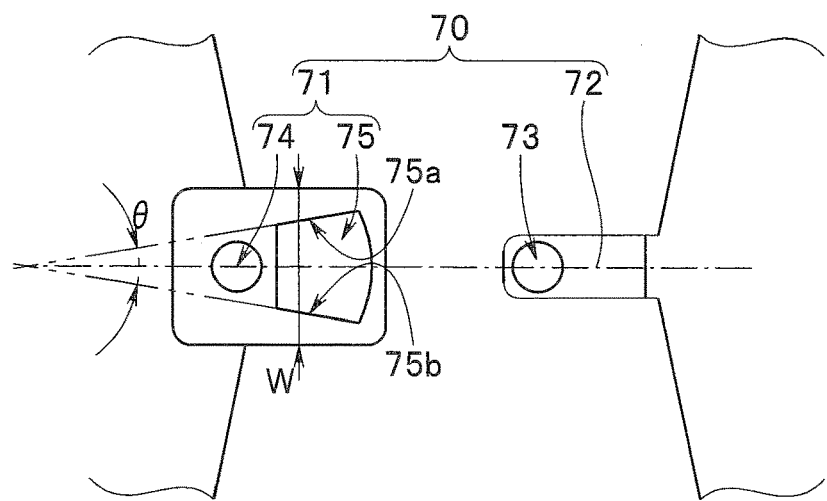
FIG. 13A is a diagram describing an example configuration of a coupling portion of a bending piece.
Figure 13B:
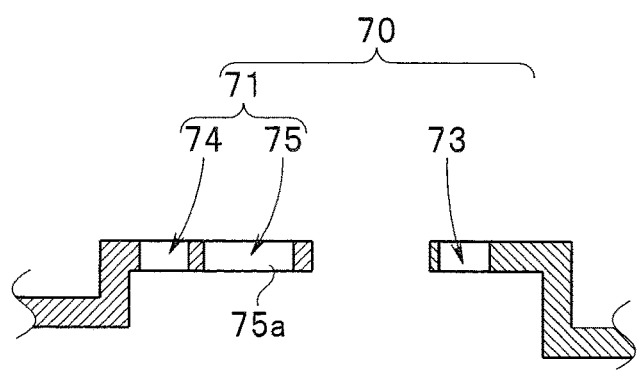
FIG. 13B is a diagram describing an example configuration of a coupling portion of a bending piece.

In the case of a configuration where facing end portions of adjacent bending pieces abut each other when the bending portion is bent, there is a possibility of an internal component of the endoscope or a mesh tube being caught between the bending pieces. Accordingly, a coupling portion 70 shown in FIGS. 13A and 13B is provided between the adjacent bending pieces of the present embodiment. The coupling portion 70 is configured from a first coupling portion 71, and a second coupling portion 72.

For example, the first coupling portion 71 is provided on the proximal end side of an intermediate bending piece, and the second coupling portion 72 is provided on the distal end side/proximal end side of the intermediate bending piece. The second coupling portion 72 includes a pin hole 73.

For its part, the first coupling portion 71 includes a pin hole 74, and a restriction hole 75. The restriction hole 75 includes a first abutting surface 75a, and a second abutting surface 75b. One side portion of a rising portion 72a of the second coupling portion 72 abuts against the first abutting surface 75a, and another side portion of the rising portion 72a of the second coupling portion 72 abuts against the second abutting surface 75b.

Figure 13C:
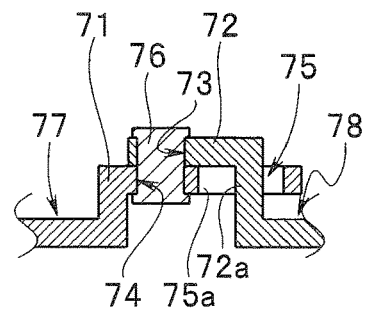
FIG. 13C is a diagram describing an example configuration of a coupling portion of a bending piece.
Figure 13D:
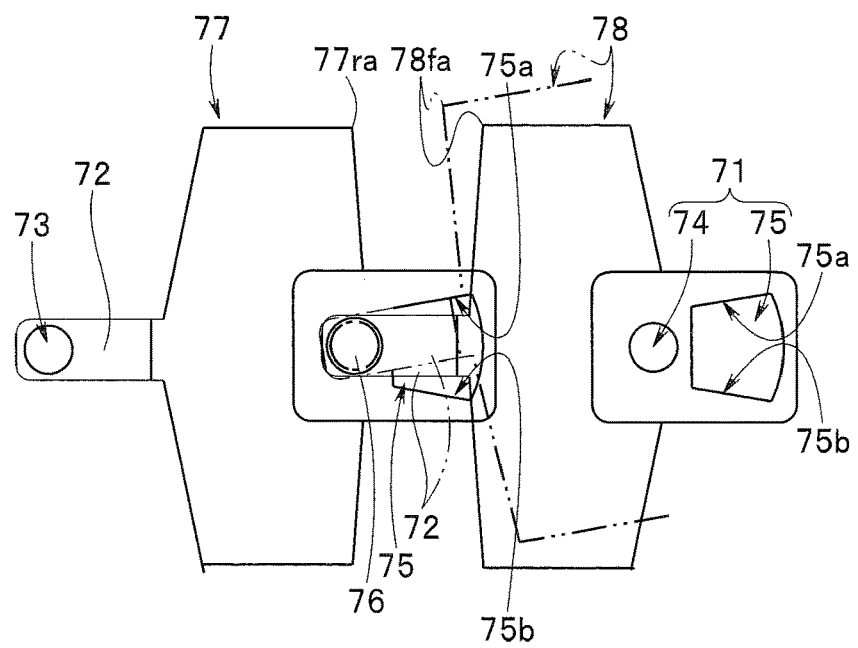
FIG. 13D is a diagram describing an example configuration of a coupling portion of a bending piece.

As shown in FIG. 13C, a coupling pin 76 is crimped while being disposed in the pin hole 73 of the second coupling portion 72 and the pin hole 74 of the first coupling portion 71. The coupling pin 76 is crimped to couple adjacent intermediate bending pieces in a rotatable state.

The rotation range of a first intermediate bending piece 77 and a second intermediate bending piece 78 which are rotatably coupled together by the coupling pin 76 is restricted by a side portion of the rising portion 72a abutting against the first abutting surface 75a or the second abutting surface 75b of the restriction hole 75.

Specifically, in a state in which one side portion of the rising portion 72a is abutting against the first abutting surface 75a of the restriction hole 75, a proximal end corner portion 77ra of the first intermediate bending piece 77 and a distal end corner portion 78fa of the second intermediate bending piece 78 do not abut against each other and are separated from each other by a predetermined distance. As a result, an inconvenience of an internal component of the endoscope or a mesh tube getting caught between the adjacent bending pieces may be prevented.

Note that the separation distance between the proximal end corner portion 77ra of the first intermediate bending piece 77 and the distal end corner portion 78fa of the second intermediate bending piece 78 may be set to achieve a desired non-abutting state by appropriately setting a width dimension W and an angle θ of the first coupling portion 71.

Note that the present invention is not limited to the embodiment described above, and may be subjected to various changes and applications within the scope of the invention.

According to the present invention, it is possible to provide an endoscope according to which pressurized air may be supplied into a space provided in the distal end portion including the raising base, which is a space where the illumination optical system and the image pickup optical system are disposed, without increasing the diameter of the insertion section including the bending portion, and according to which dust and the like in the bending portion may be prevented from entering the space and a rigid distal end portion of an endoscope.

What is claimed is:
1. An endoscope comprising:
   an operation section;
   an insertion section extending from the operation section, and including a distal end portion provided on a distal end side and a bending portion provided consecutively to the distal end portion;
   an image pickup unit disposed in the distal end portion, the image pickup unit including an observation optical system, the image pickup unit being configured to pick up an image of a subject;
   a first space formed in the distal end portion, the first space accommodating the image pickup unit, the first space including an opening of the distal end portion sealed by the observation optical system, the first space being sealed against an inner space of the bending portion to prevent fluid communication between the first space and the inner space;
   a raising base operation arm that operates a raising base, the raising base being capable of changing an advancing direction of a treatment instrument that is insertable into the insertion section;
   a second space formed in the distal end portion, the second space accommodating the raising base operation arm, the second space being sealed against the inner space of the bending portion to prevent fluid communication between the second space and the inner space;
   a raising base operation wire capable of operating the raising base operation arm, one end portion of the raising base operation wire being connected to the raising base operation arm, another end portion of the raising base operation wire being extended into the operation section;
   an elongated tube member having a through hole in a longitudinal direction, the elongated tube member having one end watertightly communicating with the second space and another end of the elongated tube member being provided inside the operation section, the raising base operation wire being inserted through the through hole; and
   a communication passage formed in the distal end portion, the communication passage watertightly communicating with the first space and with the second space.
2. The endoscope according to claim 1, wherein the tube member serves both as a wire insertion channel in which the raising base operation wire is inserted and disposed, and as a supply channel configured to supply pressurized air into the first space and into the second space through the communication passage.

3. The endoscope according to claim 1, wherein the tube member is formed only by a coil spring.

4. The endoscope according to claim 1, wherein a space volume of the communication passage is set smaller than volumes of the first space and the second space.

5. The endoscope according to claim 1, wherein the communication passage is arranged substantially perpendicularly to a long axis direction of the insertion section.

6. The endoscope according to claim 1, further comprising a signal cable connected to the image pickup unit, the signal cable extending from the distal end portion through the insertion section and into the operation section, wherein the first space is provided by sealing a space surrounding the signal cable.

7. The endoscope according to claim 6, further comprising
an illumination optical system including a light guide fiber bundle, a part of the light guide fiber bundle being accommodated in the second space, the light guide fiber bundle extending from the distal end portion through the insertion section and into the operation section,
wherein the second space is provided by sealing a space surrounding the light guide fiber bundle.

8. The endoscope according to claim 1, further comprising
a raising base space accommodating the raising base, the raising base space being formed in the distal end portion, the raising base space communicating with the second space through a shaft hole,
wherein the raising base operation arm includes a shaft portion connected to the raising base, the shaft portion being watertightly disposed in the shaft hole.

9. The endoscope according to claim 1, wherein the first space and the second space are formed isolated from an outside of the distal end portion.

10. A rigid distal end portion in an endoscope which is disposed on a distal end of an insertion section of the endoscope, comprising:
an image pickup unit disposed in the rigid distal end portion, the image pickup unit including an observation optical system, the image pickup unit being configured to pick up an image of a subject;
a first space formed in the rigid distal end portion, the first space accommodating the image pickup unit, the first space including an opening of the distal end portion sealed by the observation optical system;
a raising base operation arm that operates a raising base, the raising base being capable of changing an advancing direction of a treatment instrument that is insertable into the insertion section;
a second space formed in the rigid distal end portion, the second space accommodating the raising base operation arm;
a communication passage communicating between the first space and the second space, the communication passage being open such that fluid communication is provided between the first space and the second space,
wherein a distal end portion of an elongated tube member communicates with the second space, the tube member having a rear end portion provided in an operation section of the endoscope, a raising base operation wire capable of operating the raising base operation arm being inserted into the through hole.

* * * * *